United States Patent [19]

Groshong

[11] Patent Number: 4,772,266
[45] Date of Patent: Sep. 20, 1988

[54] CATHETER DILATOR/SHEATH ASSEMBLY AND METHOD

[75] Inventor: LeRoy E. Groshong, Portland, Oreg.

[73] Assignee: Catheter Technology Corp., Salt Lake City, Utah

[21] Appl. No.: 45,501

[22] Filed: May 4, 1987

[51] Int. Cl.⁴ ............................................. A61M 5/00
[52] U.S. Cl. ..................................... 604/164; 604/160
[58] Field of Search ..................... 604/280, 160–162, 604/164, 165, 170, 264

[56] References Cited

U.S. PATENT DOCUMENTS

Re. 31,855  3/1985  Osborne .............................. 604/161
4,596,559   6/1986  Fleischhacker .................. 604/161 X
4,650,472   3/1987  Bates ................................. 604/165 X Primary Examiner—Stephen C. Pellegrino
Attorney, Agent, or Firm—Lynn G. Foster

[57] ABSTRACT

Dilator/sheath assemblies for unstressed placement of catheter tubes into a body cavity of medical patients, which insure a stable axial relationship between concentrically superimposed sheath and dilator so that use is very facile for the medical attendent and insures a predetermined two-step gentle enlargement of a puncture site to accommodate unstressed placement of a catheter tube into a vein or artery through the puncture site and with minimal trauma to the patient.

6 Claims, 2 Drawing Sheets

CATHETER DILATOR/SHEATH ASSEMBLY AND METHOD

FIELD OF THE INVENTION

The present invention relates generally to catheter tube placement within a body cavity of a patient and more particularly to a novel removable dilator/sheath by which a soft and/or long catheter tube is introduced into a body cavity through an enlarged puncture site.

PRIOR ART

It is known to use a series of steps, including insertion of a removable dilator/sheath, to create and enlarge a puncture site into a body cavity of a patient to ultimately accommodate indwelling long term unstressed placing of a soft and/or long catheter tube, for therapeutic use. See U.S. Pat. No. Re 31,855 wherein an initially small diameter venipuncture is created by insertion of a small hollow needle into a vein. The venipuncture site is retained by insertion of a wire guide into the vein through the hollow of the needle, after which the needle is removed from the vein and the guide wire, and the wire guide is left indwelling. Next, a telescopically related hollow dilator/sheath is advanced along the guide wire and enlargingly forced through the skin, the subcutaneous tissue and the wall of the vein. The wire guide and dilator are, thereafter, telescopically removed from the venipuncture site and discarded. The catheter tube is advanced, in an unstressed condition, through the hollow of the indwelling sheath into the vein. The catheter tube is held in its indwelling location as the sheath is simultaneously manually axially separated into two halves and withdrawn from the venipuncture site. The catheter tube has a female hub at the exposed proximal end thereof. The sheath has an axial molecular orientation or other means such as two prescored lines which accommodates the mentioned manual axial separation of the sheath into two parts to remove the sheath from its prior superimposed telescopic disposition upon the catheter tube.

With dilator/sheath devices typified by that disclosed in U.S. Pat. No. Re 31,855, there is a tendency for the dilator to telescopically retract within the sheath when the medical attendant, nurse, doctor or the like is attempting to forcibly enlarge the venipuncture site by driving the tapered leading tip of the dilator through the epidermis, subcutaneous tissue and the wall of the vein. This makes manipulation of the dilator/sheath not only traumatic to the patient, but also awkward and imprecise for the medical attendant. When the dilator recedes entirely to a position within the sheath, the venipuncture enlargement caused by entry of the relatively large tapered distal end of the sheath through the venipuncture site is painfully traumatic to the patient and risks tearing of the tissue adjacent the venipuncture and may allow the sheath to bend or kink forcing abandonment of that site and de novo selection and creation of a new venipuncture site for long-term indwelling catheter tube purposes.

BRIEF SUMMARY AND OBJECTS OF THE INVENTION

In brief summary, the present invention comprises dilator/sheath assemblies, and related methods, used in unstressed placement of catheter tubes into body cavities of medical patients, which invention overcomes or substantially alleviates the aforementioned problems of the prior art. The present invention insures a stable axial relationship between the superimposed sheath and dilator so that use is very facile for the medical attendant and insures a predetermined two-step gentle enlargement of the puncture site to accommodate unstressed placement of a soft and/or long catheter tube in the vein through an undamaged enlarged puncture site and with minimal trauma to the patient.

It is, accordingly, a primary object of the present invention to provide a novel dilator/sheath device, and related methods.

A further significant object of the present invention is a provision of an improved dilator/sheath device used in the unstressed placement of tubes into body cavities of medical patients.

It is a further dominant object of the present invention to provide a novel dilator/sheath device which insures a stable relationship between the superimposed sheath and dilator during insertion.

It is an additional important object of the present invention to provide an improved dilator/sheath device whereby use thereof is very facile for the medical attendant and insures a predetermined two-step low trauma enlargement of the puncture site to accommodate unstressed placement of a soft and/or long catheter tube in a body cavity through the puncture site without causing damage to the puncture site.

These and other objects and features of the present invention will be apparent from the detailed description taken with reference to the accompanying drawings.

DETAILED DESCRIPTION OF THE ILLUSTRATED EMBODIMENTS

Figure 1:
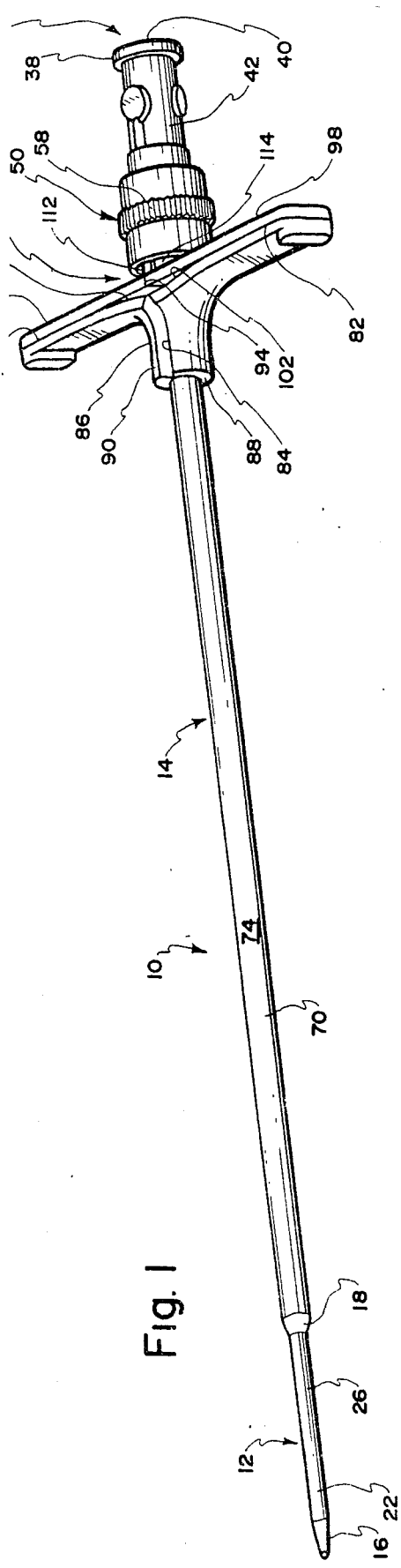
FIG. 1 is a perspective representation of a presently preferred dilator/sheath assembly embodying the principles of the present invention.

Reference is now made to the drawings wherein like numerals are used to designate like parts throughout. Specific references made to FIGS. 1-5, which illustrate a presently preferred dilator/sheath assembly, generally designated 10. The dilator/sheath assembly 10 broadly comprises a dilator, generally designated 12, and a sheath 14. The objective of the dilator/sheath assembly 10, is to use the same in the assembled condition shown in FIG. 1 by advancing the assembly 10 telescopically over a guide wire indwelling in a vein, an artery or other body cavity of a medical patient and to force first the tapered distal end 16 of the dilator 12 through the puncture site to enlarge the same and thereafter to likewise force the tapered distal end 18 of the sheath assembly 14 through the puncture site to further enlarge the same, all preparatory to insertion of a flexible catheter tube 20 (FIG. 5) through the hollow interior of the sheath while the sheath is indwelling, in a manner hereinafter explained in greater detail. As also explained more specifically herein, the dilator 12 is later withdrawn from the puncture site and the sheath is subsequently removed from the indwelling flexible catheter tube 20.

The dilator 12 comprises a hollow cannula 22 which defines an internal bore 24 of diametrical dimensions greater than the diameter of the guide wire over which the dilator/sheath assembly 10 is inserted through the puncture site into the desired vein, artery or other body cavity. The bore 24 is illustrated as being uniform throughout the length thereof, except for a divergent conically-shaped internal taper at the distal end 16 thereof and the proximal end thereof. The cannula 22 is illustrated as comprising a wall of uniform thickness comprising an external cylindrical surface 26, which also comprises uniform diameter. The cannula 22 is preferably formed of a rigid, shape-retaining plastic, which will not buckle under the manual force required to displace the dilator/sheath assembly 10 through the puncture site into the vein, artery or other body cavity of the patient. Polytetrafluoroethylene is suitable.

The proximal end of the cannula 22 comprises a blunt transverse edge 30.

A hollow fitting or collar 34 is concentrically and essentially contiguously superimposed around the exterior surface 26 of the cannula 22 at the proximal end thereof and is secured in said position by a suitable bonding agent or adhesive applied at the interface site 36 between these two components of the dilator 12. The interior 36 of the collar 34 is stepped at shoulder 37 to a reduced diameter size shown to be equal to the diameter of the cannula bore 24. The interior of the collar 34 proximal of the shoulder 37 comprises a rearwardly divergent conical female opening 28 which merges with both the shoulder 37 and the blunt transverse edge 40. See FIG. 3. To prevent contamination, the conical entryway 28 may be plugged during periods of storage and nonuse. The fitting 34 comprises a proximal luer loc flange 38 and a blunt face 40 transversely disposed to the axis of the cannula 22.

The fitting 34 comprises a central body 42 of any desired configuration by which the medical attendant, nurse, doctor or the like may grip the fitting 34 and manually manipulate the dilator 12 so as to enlarge the puncture site, as stated, and telescopically separate the dilator 12 from the sheath 14. The proximal end collar 34 terminates in an annular forward ring 44. Annular forward ring 44 comprises a tapered exterior surface 46 and a rounded transverse forward edge 48.

A female generally annular coupling member, generally designated 50, is integrally joined to the forward annular ring 44 at tapered surface 46 by application of a suitable adhesive or bonding agent at tapered opening 54. The female coupling member 50 comprises an inwardly-directed radial flange 52 which defines the tapered opening 54, which is essentially contiguous with the surface 46 of the annular segment 44 where the adhesive at site 54 joins the two into integral nonrotatable relation.

The female coupling member 50 further comprises a substantially uniform exterior cylindrical surface 56, interrupted by a knurled or similar type of gripping annular surface 58 located annularly along the central part of the exterior surface 56. The internally-directed flange 52 comprises exposed radially-directed surface 53 and a concealed radially-directed surface 55. Thus, the inwardly-directed radial flange 52 is illustrated as having a uniform thickness.

The female coupling member 50 terminates in a forward blunt edge 60. The interior of the hollow female coupling member 50 comprises a substantially uniform cylindrical surface 62, which is interrupted by a helically-directed luer loc thread 64, which projects inwardly. The diameter of surface 62 is substantially greater than the outside diameter of cannula 22. As hereinafter explained in greater detail, the female coupling member 50 is adapted to create a releasable but locked relationship between the dilator 12 and the sheath 14 so that the two function unitarily during insertion of the device 10 through the puncture site to enlarge the same on a two-step, sequential basis.

Sheath 14 comprises an external cannula 70, which defines a central hollow interior 72 illustrated as being of uniform diameter throughout the entire length of the cannula 70 except for the conical taper at distal tip 18 and the proximal end. The wall of the cannula 70 is illustrated as being of uniform thickness, thereby defining a uniform diameter exterior cylindrical surface 74. The axial length of the cannula 70 is of a predetermined distance, somewhat less than the length of the dilator cannula 22, to provide for the stepped enlargement of the puncture site, as mentioned earlier.

The diameter of the bore 72 is illustrated as being substantially the same as the diameter of the dilator cannula external surface 26, accommodating contiguous telescopic axial insertion of the dilator cannula 22 into and contiguous telescopic removal of cannula 22 from the sheath cannula 70. The cannula 70 is preferably formed so that it is manually axially severable into two halves. This may be accomplished by either a molecular orientation, as set forth in U.S. Pat. No. Re 31,855, or may be mechanically achieved by placing opposed grooves or tear lines in the wall of the cannula 74. However, a sheath which is not severable into two halves may be used when the catheter tube is not encumbered by a fitting on the proximal end thereof, thereby accommodating axial removal of the entire sheath from the catheter tube at the appropriate time.

Figure 3:
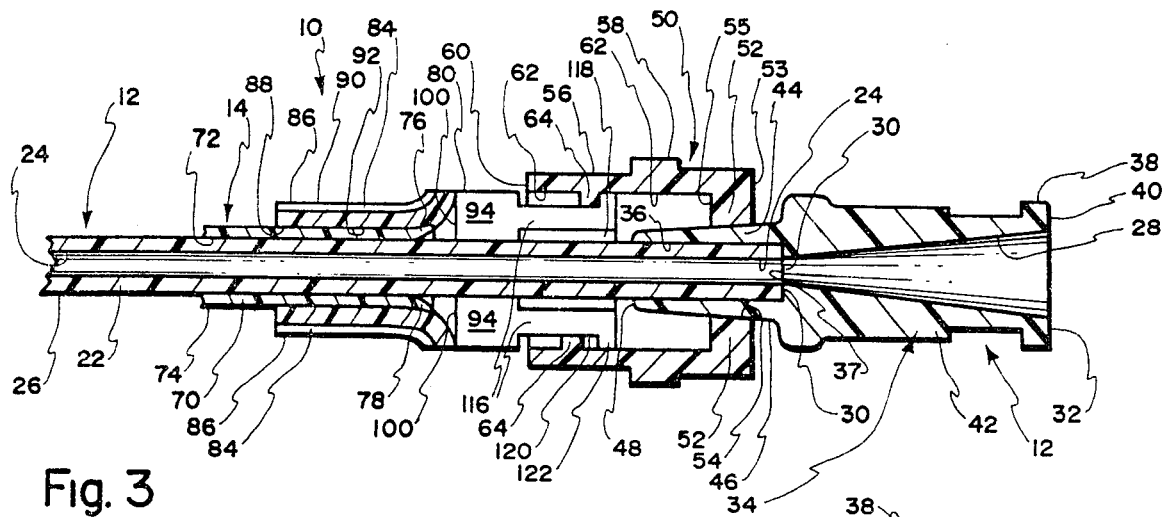
FIG. 3 is a fragmentary cross-section taken along lines 3—3 of FIG. 2.
Figure 4:
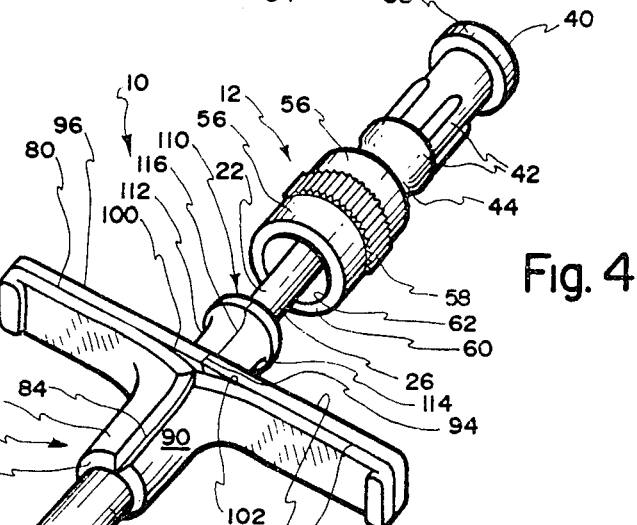
FIG. 4 is a fragmentary perspective of the proximal end of the assembly of FIG. 1, similar to FIG. 2, but illustrating the dilator partially withdrawn from its telescopic relation with the sheath of the assembly of FIG. 1.

Cannula 70 is illustrated as comprising opposed proximal end ears 76 and 78, which project divergently outward from the dilator cannula 22 and are respectively connected in such a way as to accommodate the axial tearing of the cannula 70 into two parts. The proximal end tabs 76 and 78 are internally concealed as illustrated in FIG. 3.

The proximal end of the sheath 14 comprises opposed transversely-directed tabs 80 and 82, whiCh are seVerably joined one to another along opposed reduced thickness weakened grooves 84. See FIG. 3. The tabs 80 and 82 are formed of rigid shape-retaining material and jointly merge into a collar 86 in which the aforementioned weakened grooves 84 are disposed. The collar 86 otherwise comprises an annular wall of substantially uniform thickness comprising an internal cylindrical surface 88, the diameter of which is substantially the same as the exterior diameter of the outside surface 74 of the cannula 70. The collar 86 is secured by placement of a suitable bonding agent or adhesive disposed at site 92 comprising the interface of the essentially contiguous surfaces of 88 and 74. See particularly FIG. 3.

The collar 86 also defines a substantially uniform exterior cylindrical surface 90 which merges, on a contoured basis, into the transversely-directed opposed gripping tabs 80 and 82. The tabs 80 and 82 are integrally joined respectively to the sheath cannula ears 76 and 78. The tabs 80 and 82 are also joined one to another directly adjacent the collar 86 but accommodate manual severance of one from each other with the aid of an axially-directed slit 94, which extends rearwardly from the proximal end of each weakened groove 84 to the trailing transverse surfaces 96 and 98 of the transverse tabs 80 and 82, respectively, and extends entirely through the tabs 80 and 82 from top to bottom, as illustrated.

The slit 94 merges with opposed transverse slits 100 and 102, which extend entirely through the tabs 80 and 82, respectively, and merge with the slit 94. Slits 100 and 102 extend only part way into the body of the tabs 80 and 82, respectively. Therefore, when the tabs 80 and 82 are firmly manually pulled outwardly and toward the leading end 18 of the sheath 14, sufficient force will be generated to axially sever the collar 86 into two parts along the grooves 84 and thereafter to similarly axially sever the cannula 70 into two halves.

The tabs 80 and 82 also comprise opposed semi-circular or semi-annular halves of a proximal male coupling member, generally designated 110. The semi-annular halves 112 and 114 are identical but of opposite hand. They are separated one from the other by an axial top and bottom slits at sites 116. The two halves 112, 114 mate one with another to form the generally annular male coupling member 110. Together they define a substantially uniform inside cylindrical surface 118 of uniform diameter, illustrated as being slightly larger than the outside diameter of cannula 22, and an outside cylindrical surface 120 of substantially uniform diameter.

Figure 2:
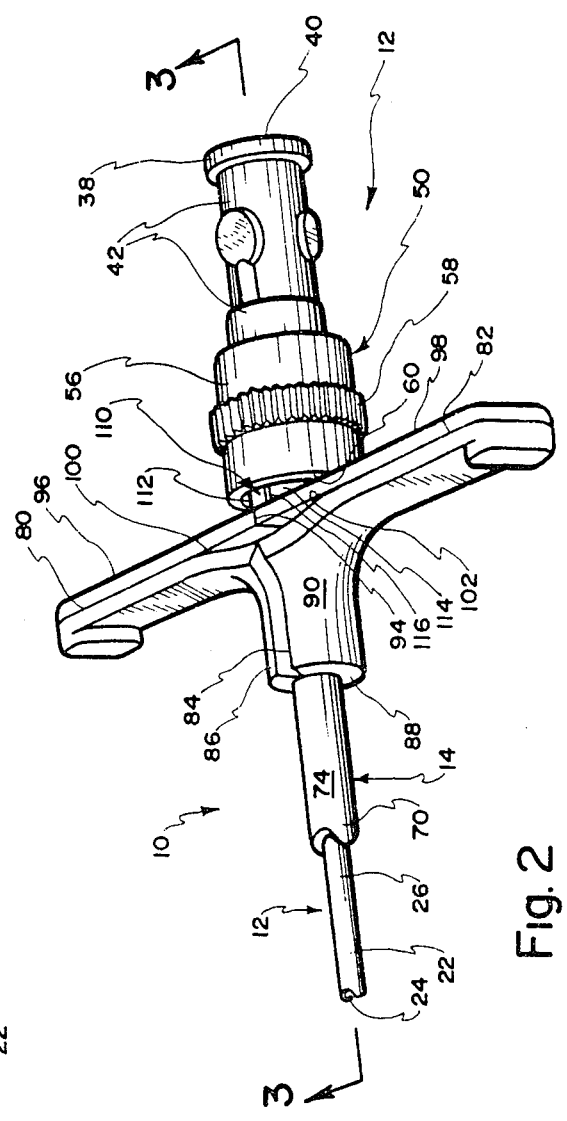
FIG. 2 is an enlarged fragmentary perspective of the proximal end of the dilator/sheath assembly of FIG. 1.

Surface 120 is interrupted by a radially-directed luer loc flange 122, sized and shaped so as to accommodate a luer loc releasable connection between the luer loc flange 122 and the luer loc thread 64 of the female coupling member 50. Ordinarily, rotation of approximately 90° is all that is required to create the assembled axially locked relationship between the dilator and the sheath, as illustrated in FIGS. 1, 2 and 3. Thus, the device 10 functions unitarily without risk of relative axial displacement between the dilator 12 and the sheath 14. Likewise, opposite rotation of essentially 90° will separate the female coupling member 50 from the male coupling member 110 to accommodate thereafter telescopic withdrawal oi the dilator 12 from the sheath 14. See FIG. 4.

Figure 5:
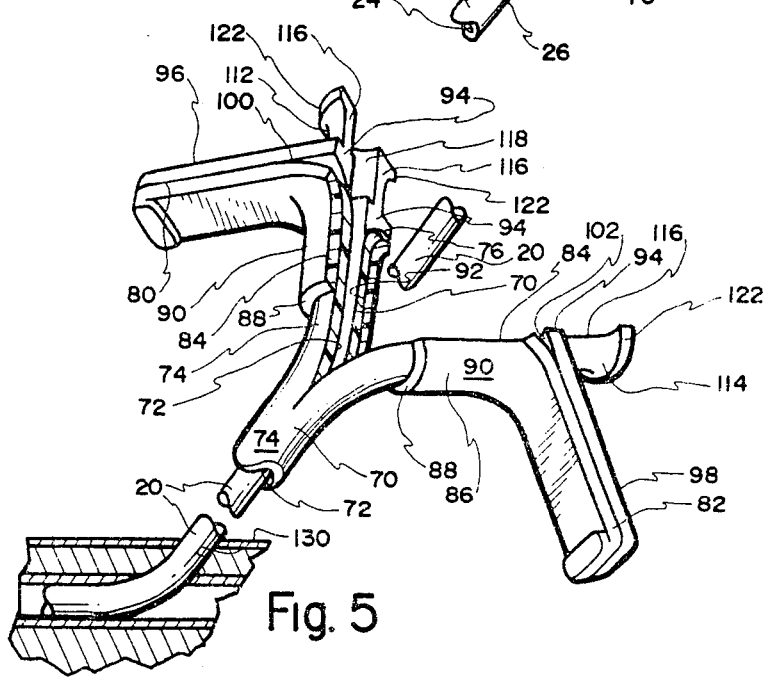
FIG. 5 is an enlarged fragmentary perspective of the sheath of the dilator/sheath assembly of FIG. 1 partially axially torn during the process of removing the sheath from a superimposed relationship around an indwelling catheter tube.

With the sheath assembly 14 indwelling through the puncture site into a vein or artery and the dilator 12 removed, in the manner described, the catheter tube 20 is manually advanced through the hollow passageway 72 of the cannula 70 of the sheath 14 until the catheter tube 20 is suitably indwelling in the vein, artery or other body cavity of the patient through the puncture site 130, as illustrated in FIG. 5. The medical attendant holds the catheter tube 20 in its indwelling location and the sheath 14 is preferably simultaneously removed from the puncture site and the sheath 14 is manually torn into two axially-separated halves by oppositely pulling on tabs 80 and 82. The sheath 14 is illustrated in a partially severed condition in FIG. 5.

The dilator 12 and the severed halves of the sheath 14 are discarded. The catheter tube 20 is left indwelling for suitable therapy as medically indicated.

Figure 6:
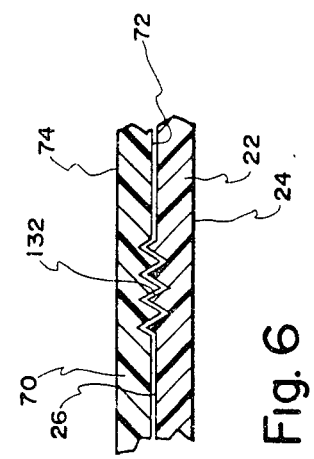
FIG. 6 is a fragmentary enlarged cross-sectional view of the superimposed dilator and sheath stably secured one to another by an internal threaded relationship.

Reference is now made to FIG. 6 which illustrates a second presently preferred embodiment in accordance with the present invention wherein in lieu of the male-female coupling members 50, 110 a threaded relation at site 132 between the contiguous external surface 26 of the fully inserted cannula 22 and the internal surface 72 of the cannula 70 so as to insure unitary insertion of the dilator cannula and the sheath cannula, following whiCh the dilator cannula and the sheath cannula may be threadedly uncoupled to accommodate axial removal of the dilator from the sheath in the manner heretofore described.

The invention may be embodied in other specific forms without department from the spirit or essential characteristics thereof. The present embodiments, are, therefore, to be considered in all respects as illustrative and not restrictive, the scope of the invention being indicated by the appended claims rather than by the foregoing description, and all changes which come within the meaning and range of equivalence of the claims are therefore to be embraced therein.

What is claimed and desired to be secured by United States Letters Patent is:

1. A dilator/sheath assembly for enlargement of a puncture site into a desired location within the body of a patient, the dilator/sheath assembly comprising:
   dilator means comprising an elongated dilator cannula adapted to telescopically receive an indwelling guide wire, the dilator cannula comprising a tapered distal end and proximal end of means;
   sheath means comprising an elongated sheath cannula comprising opposed sheath halves connected to each other along two longitudinally directed weakened tear line means, the sheath cannula adapted to be concentrically contiguously removably disposed upon the dilator cannula in the assembled condition, the sheath cannula comprising a tapered distal end, the axial length of the elongated sheath cannula being less than the axial length of the dilator cannula so that the tapered distal ends of the two cannulas are disposed in tandem relation for two-stepped sequential enlargement of the puncture site, the hollow of the sheath cannula being sized to accommodate placement of a pliant catheter tube therethrough into a desired body location when the sheath cannula is located in the puncture site and the dilator means are removed from the sheath means, the halves of the sheath cannula at the proximal end thereof being split into two separate tabs and the proximal end of the sheath means comprising two handles, one attached to each tab, by which the sheath cannula, while surrounding the indwelling catheter tube, is manually caused to be severed along the tear line means into two parts;
   connector means releasibly locking the dilator means to the split proximal end of the sheath means against inadvertent relative axial displacement and also releasibly securing the separate tabs and handles together for initial unitary action whereby said successive enlargements of the puncture site by sequential entry of the distal ends with the two cannulas are assured followed by disconnection of the connector means, removal of the dilator means, insertion of the catheter tube through the hollow of the sheath cannula, removal of the distal end of the sheath cannula from the puncture site, and tearing of the sheath cannula into two halves while surrounding the indwelling catheter tube.

2. A dilator/sheath assembly according to claim 1 wherein the connector means comprise manually interlockable and manually releasible female and male means carried respectively by the proximal end of the dilator means and the proximal halves of the sheath means.

3. A dilator/sheath assembly according to claim 1 wherein the connector means comprise manually interlockable and releasible female and male means carried at the respective exposed proximal end of the dilator means and the proximal halves of the sheath means.

4. A dilator/sheath assembly according to claim 1 wherein the connector means comprise manually manipulable interlockable and releasible male/female means carried by the proximal end of the dilator means and proximal halves of the sheath means in concealed relation when the dilator/sheath assembly is fully assembled.

5. A dilator/sheath assembly according to claim 4 wherein the concealed male/female means comprise interlocking opposed threads carried at inside surfaces of the proximal halves of the sheath means and the outside surface of the proximal end of the dilator cannula.

6. A method of placing a catheter tube indwelling within a desired body site of a medical patient without subjecting the catheter tube to stress, comprising the steps of:

creating a relatively small puncture site through the epidermis, subcutaneous tissue and into a desired body cavity;

placing the distal end of a guide wire or the like indwelling at the body site through the puncture site, with the proximal end of the guide wire exposed outside the patient;

releasibly locking the proximal end of a dilator of a dilator/sheath assembly to opposed separate proximal end parts of a sheath of the assembly against relative axial displacement;

telescopically advancing the assembly over the proximal end of the guide wire;

manually forcing first the distal end of the dilator and thereafter the distal end of the sheath through the puncture site, while obviating relative axial movement between the dilator and sheath, to sequentially diametrically enlarge the puncture site without tearing or otherwise damaging the same;

removing the guide wire from the patient while preserving the distal end of the sheath in its indwelling condition;

releasing the locked condition between the proximal end of the dilator and the opposed separate proximal end parts of the sheath and telescopically removing the dilator from the patient and the sheath, while retaining the distal end of the sheath in its indwelling condition;

telescopically advancing the catheter tube, without imposing material stress thereon through the partially indwelling sheath until the distal end of the catheter tube is indwelling at the body site;

telescopically retracting the sheath from its indwelling disposition along the catheter tube;

manually grasping the opposed separate proximal end parts of the sheath while the sheath is telescopically superimposed upon the catheter tube and axially tearing the sheath into two disposable separate pieces;

using the indwelling catheter tube for medical therapy.

* * * * *